United States Patent [19]
Boate et al.

[11] Patent Number: 5,220,106
[45] Date of Patent: Jun. 15, 1993

[54] ORGANIC NON-QUATERNARY CLATHRATE SALTS FOR PETROLEUM SEPARATION

[75] Inventors: Douglas R. Boate, Sarnia, Canada; Michael J. Zaworotko, USAF Academy, Colo.

[73] Assignee: Exxon Research and Engineering Company, Florham Park, N.J.

[21] Appl. No.: 858,455

[22] Filed: Mar. 27, 1992

[51] Int. Cl.$^5$ .................................................. C07C 7/10
[52] U.S. Cl. ...................................... 585/865; 585/860; 585/864
[58] Field of Search .......................... 585/860, 864, 865

[56] References Cited

U.S. PATENT DOCUMENTS

| | | | |
|---|---|---|---|
| 4,075,170 | 2/1978 | Ponomarev et al. | 260/45.6 G |
| 4,321,127 | 3/1982 | Atwood | 208/435 |
| 4,359,596 | 11/1982 | Howard et al. | 585/856 |
| 4,422,975 | 12/1983 | Mitchell | 260/448 |
| 4,440,634 | 4/1984 | Mitchell | 208/310 |

FOREIGN PATENT DOCUMENTS

| | | |
|---|---|---|
| 2123138 | 9/1972 | France. |
| 2123139 | 9/1972 | France. |
| 2123140 | 9/1972 | France. |
| 7034029 | 10/1970 | Japan. |
| 82418 | 4/1986 | Japan. |
| 127115 | 6/1986 | Japan. |

OTHER PUBLICATIONS

"Equilibrium of Liquid phases in the triethylamine-water-salicylic acid system" Erofeeva, et al. Uch. Zap. Perm. Gas Univ. 1966, No. 159, 46–53.

"Determination of dissociation constants of organic acid salts in acetronitrile by a potentiometric method" Kreshkov et al. Zh Fix Khim, 1974, 48(2) 459–61.

"Synthesis of Water Soluble Cutting Fluids" Suga et al. Kankyo Kagaku Kenkyu Hokoku (Chiba Daigaku) 1977–78 (Published 1979), 15–16.

"Chemistry of organic fluorine compounds, XXIII, Synthesis and biological activity of halofluoroacetylsalicyclic acid" Liska et al. Sb. Vys. Sk. Chem-Technol. Praze. Org. Chem. Technol, 1982, C27, 21–8.

"Spectral characteristics of the infrared bands r(OH) and r(NH+) of H-complexes of carboxylic acids and nitrogen bases with strong hydrogen bonding and proton transfer" Glazunov, et al. Zk. Prikl Spektrosk, 1975 23(3) 469–74.

"Halogen complexes of pyridines. A proton and carbon-13 nuclear magnetic resonance study" Schuster et al. J. Org. Chem 1979, 44(15) 2658–62.

"Hydrogen-bonded ionic species of pyridinium trifluoroacetates. I. Conductance behavior in various solvents" Mahta et al. Electrochim Acta, 1982 27(1) 9–13.

"Hydrogen-bonded species of pyridinium halo acetates. 2. Thermometric behavior in aprotic solvents" Chawla, et al. J. Phys. Chem 1984. 88(12) 2650–5.

"Infrared investigation of hydrogen bonding and proton transfer of some pyridine trifluoroacetates in benzene" Dega-Szafran et al. J. Chem Soc. Perkin Trans. 2, 1982(2) 195–8.

"Infrared spectra of some pyridine trifluoroacetates in benzene and dichloromethane" Daga-Szafran, et al. J. Chem Soc. Chem Commun 1984 (22) 1470–2.

"Spectroscopic differences between molecular (OH ... N) and ionic pair (O$^-$ ... NH$^+$) hydrogen complexes". Barczynski et al. J. Chem. Soc. Perkin Trans. 2 1985 (6) 765–71.

"Interaction of 2,4,6-trimethylpyridine with some halo carboxylic acids in benzene and dichloromethane. Problem of Stoichiometry" Barczynski et al. J. Chem Soc. Perkin Trans. 2. 1987 (7) 901–6.

"Reactions of allylstannance with in-situ generated immonium salts in protic solvent; a facile aminomethanodestannylation process" Grieco, et al. J. Org. Chem. 1987, 52(7) 1378–80.

"Hydrogen transfer from tertiary amines to trifluoroacetic anhydride", Schreiber, Tetrahedron Lett, 1980, 21(11) 1027–30.

Primary Examiner—Anthony McFarlane
Attorney, Agent, or Firm—Joseph J. Allocca

[57] ABSTRACT

Organic non-quaternary clathrate salts are useful for separating hydrocarbon feed streams into aromatics rich fraction and aromatics lean fraction. The organic non-quaternary clathrate salts are characterized by having cations containing less than 16 carbon atoms. Preferred salts are collidinium triflate and triethylammonium dihydroxybenzoate.

10 Claims, No Drawings

ORGANIC NON-QUATERNARY CLATHRATE SALTS FOR PETROLEUM SEPARATION

BACKGROUND OF THE INVENTION

1. Field of the Invention

Hydrocarbon feed streams containing mixtures of aromatic hydrocarbons and non-aromatic hydrocarbons are separated into aromatics lean streams and aromatics rich streams by contacting the hydrocarbon stream with an organic non-quaternary clathrate salt having a cation containing less than 16 carbon atoms. The clathrate salts selectively interact with the aromatic components of the hydrocarbon feed mixture. The organic non-quaternary clathrate salt possess non-quaternary cations such as phosphonium, ammonium, imidazolium, pyridinium and piperidinium and a monovalent or polyvalent anion. They can be represented by formula:

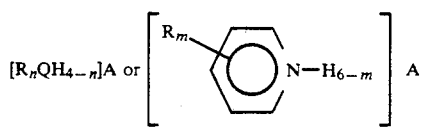

wherein

R is a radical independently selected from the group consisting of hydrogen, linear or branched $C_1$-$C_{12}$ alkyl, $C_5$-$C_{12}$ cycloalkyl, $C_7$-$C_{12}$ aralkyl and alkaryl and $C_6$-$C_{10}$ aryl, including inert or unreactive substitutes therein and mixtures thereof, wherein the total number of carbon atoms in the total of the R radicals in the cation is less than 16;

n is 1-3;
m is 1-5;
Q is N or P;
A is a monovalent or polyvalent anion.

The separation is conducted either above the melting point of the clathrate salt but below the decomposition temperature of either the salt or the hydrocarbon feed or under conditions such that the salt goes into solution in the hydrocarbon feed. The clathrate salt is separated from the aromatic hydrocarbon with which it combines by e.g. washing with water.

2. Description of the Related Art

U.S. Pat. No. 4,359,596 describes the separation of aromatics from mixed aromatics/aliphatics hydrocarbon streams by liquid salt extraction. The liquid salts used are of the formula

[R$_4$Q][A]

wherein

Q is nitrogen, phosphorous or arsenic;
A is a monovalent or polyvalent anion;
R$_4$Q is a monovalent or polyvalent cation in sufficient numbers to render the salt electrically neutral;
R is a hydrocarbon radical independently selected from the group consisting of linear or branched $C_1$-$C_{20}$ alkyl, $C_5$-$C_{10}$ cycloalkyl, $C_7$-$C_{20}$ aralkyl and alkaryl, and $C_6$-$C_{10}$ aryl, concluding inert or unreactive substitutes therein and mixtures thereof, wherein the total number of carbon atoms in the four R radicals totals at least 16 and wherein not more than one R radical is methyl. The separation is performed by contacting the hydrocarbon feed with the salt above the melting point but below the decomposition point of the liquid salt.

The salt is seen to possess a cation which is quaternary and contains at least 16 carbon atoms.

SUMMARY OF THE INVENTION

Aromatic hydrocarbons are separated from hydrocarbon feed streams comprising mixtures of aromatic hydrocarbons and non-aromatic hydrocarbons by contacting the hydrocarbon feed with an organic nonquaternary clathrate salt having a cation containing less than 16 carbon atoms. The organic non-quaternary clathrate salt selectively combines with the aromatic hydrocarbons in the feed and produces a binary liquid-liquid phase system, i.e., a raffinate phase of reduced aromatic content and an extract phase of increased aromatic content containing the aromatic hydrocarbon combined with the clathrate salt. The raffinate and extract phases are separated, then the aromatic hydrocarbon-clathrate salt combination is itself separated into an aromatics rich stream and a recovered organic non-quaternary clathrate salt stream, which is recycled to the separation.

The organic non-quaternary clathrate salt possesses as non-quaternary cations such cations as ammonium, phosphonium, pyridinium, imidazolium, and piperdinium, preferably ammonium and pyridinium, and a monovalent or polyvalent anion.

The salts can be represented by the following formula:

[R$_n$QH$_{4-n}$][A], 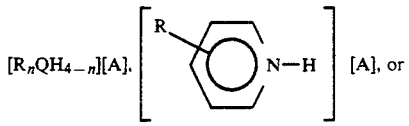

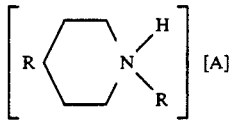

wherein

Q is nitrogen, phosphorus, or arsenic;
R is hydrogen, $C_1$-$C_{12}$ linear or branched alkyl, $C_5$-$C_{12}$ cycloalkyl, $C_7$-$C_{12}$ aralkyl or alkaryl, and $C_6$-$C_{10}$ aryl, including inert or unreactive substances including heteroatom containing species such as alkoxy, and mixtures thereof, wherein the total number of carbon atoms in the sum of the R radical groups in the cation is less than 16;
n is an integer ranging from 1-3;
A is a monovalent or polyvalent anion.

The separation of aromatic hydrocarbons from the hydrocarbon feeds is performed by contacting the hydrocarbon feed with the organic non-quaternary clathrate salt either above the melting point of the salt but below the decomposition temperature of either the salt or the hydrocarbon feed or under conditions such that the solid salt goes into solution in the hydrocarbon feed.

DETAILED DESCRIPTION OF THE INVENTION

Aromatic hydrocarbons may be selectively separated from hydrocarbon feeds comprising mixtures of aromatic hydrocarbons and non-aromatic hydrocarbons by contacting hydrocarbon feed with an organic clathrate salt having a non-quaternary cation possessing less than 16 carbon atoms.

The process is useful in treating lube stocks for the removal of aromatics to produce aromatics lean raffinates or for the recovery of aromatics such as benzene, toluene and xylene in chemical feed streams.

The separation employs a organic clathrate salt having a non-quaternary cation possessing fewer than 16 cation atoms. The salt may be a "liquid salt" by which is meant a molten fluid at the temperature of extraction, from about room temperature (approximately 20° C.) to about 400° C., preferably about 20° C. to 200° C., in which the solvent is present above its melting point but below the decomposition temperature of either the salt or the hydrocarbon feed.

When used as a liquid salt the liquid salt can be a clear, pourable fluid or a melt. The salt can be a solid provided it goes into solution in the hydrocarbon feed under the conditions employed.

Contacting the salt with the hydrocarbon feed permits the salt to combine with the aromatic hydrocarbons present in the feed to produce a binary liquid-liquid phase system. The extract phase of salt plus aromatics is usually the more dense phase and exists either as a separate distinct lower phase or as suspended droplets in a continuous lighter phase (the raffinate).

The process of the present invention employs organic nonquaternary salts which may be represented by the following formula:

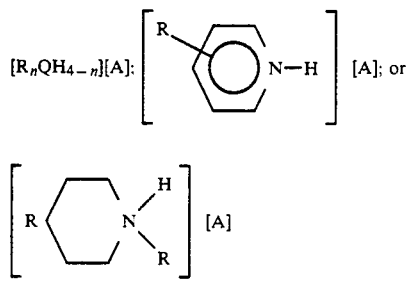

wherein

Q is nitrogen, phosphorus, or arsenic;

R is hydrogen, $C_1$-$C_{12}$ linear or branched alkyl, $C_5$-$C_{12}$ cycloalkyl, $C_7$-$C_{12}$ aralkyl or alkaryl, and $C_6$-$C_{10}$ aryl, including inert or unreactive substances including heteroatom containing species such as alkoxy, and mixtures thereof, wherein the total number of carbon atoms in the sum of the R radical groups in the cation is less than 16;

n is an integer ranging from 1-3;

A is a monovalent or polyvalent anion present in sufficient number to balance the electrical charge of the cation.

Representative R radicals in the cation include methyl. ethyl, propyl, n-butyl, sec-butyl, t-butyl, n-pentyl, 2 methylbutyl, 3-methylbutyl, n-hexyl, n-octyl, 2-ethylhexyl, decyl, stearyl, cyclohexyl, p-chlorobenyl, benzyl, p-methylbenzyl, 2-phenethyl, tolyl, p-xylyl, phenyl, chlorophenyl, dodecyl, trifluorobutyl, n-eicosonyl, cyclohexylbutyl, phenylbutyl, butylphenyl, naphthyl and the like. The R radical may also be substituted with substituents inert under the process condition such as $C_1$-$C_{12}$ alkoxy, $C_6$-$C_{10}$ aryloxy and the less reactive halogens fluorine and chlorine.

Representative cations include triethylammonium, lutidinium, collidinium, 2-ethyl pyridinium, 2-ethoxy pyridinium, 1-methyl piperidinium, piperidinium, 1-ethylcollidinium, 1-methyl, 3-ethylimidazolium, 1-methylimidazolium.

Anions may be any of the typical anions common to salt formation including carboxylates, benzoates, sulfonates and derivatives thereof, e.g.:

where R is OH, $C_1$-$C_{10}$ alkyl, $C_1$-$C_{10}$ alkoxy, n=0.5.

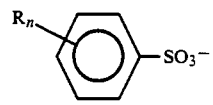

wherein R is OH, $C_1$-$C_{10}$ alkyl, $C_1$-$C_{10}$ alkoxy, n=0.5.

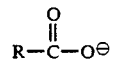

wherein R is H, $CF_3$, $C_1$-$C_{10}$ alkyl. Other typical anions include (fluoride, chloride, bromide, iodide, sulfate, naphthenate, bicarbonate, bisulfide, nitrate, halometallate (e.g., tetrafluoro-borate) methanesulfonate, trifluorormethanesulfonate, dodecylsulfonate, phosphonate, benzenephosphonate, tetra-n-butylboranate, acetate and 2-ethylthexanoate, benzenesulfonate, p-toluenesulfonate, p-chlorobenzenesulfonate, phenoxybenzenesulfonate, benzenephosphinate, benzoate, tetrachloroaluminate, tetrafluoroborate, hydroxide, methoxide, phenoxide, 2,4,6-tri-t-butylphenoxide, tris(2-methoxyethoxy)acetate, tetra-2-ethylhexylboranate, tetra-sec-butylboranate, triethyl-2-ethylhexylboronate, and the like. Particular examples include salicylate, triflate, 2,6-dihydroxy benzoate.

The organic non-quaternary clathrate salts useful in the present invention are synthesized by techniques common to the art. The appropriate organic base is reacted with the appropriate organic acid in a suitable solvent such as tetrahydrofuran (THF), or the reaction can be run neat (in the absence of solvent) if one or both of the acid or base is liquid.

Preferred organic non-quaternary clathrate salt include triethylammonium salicylate, lutidinum triflate, collidinium triflate

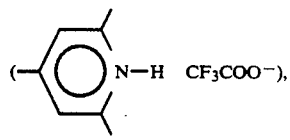

2-ethylpyridinium triflate, 2 ethoxypyridinium triflate, 1-methylpiperidinium triflate, triethylammonium 2,6dihydroxybenzoate, piperidinium triflate, tripropyl ammonium formate, 1-methyl piperidinium phenylacetate, triethyl ammonium m-nitrobenzoate, quinolinium triflate.

The extracting solvent in this process comprises an organic non-quaternary salt and can also include a small quantity of cosolvent or cosolvents for the liquid salt, such as water, acid, alcohol, or the corresponding acid of the anion radical. Water is especially useful because it is inexpensive, relatively non-corrosive and can increase selectivity in the extraction; however, the use of water does diminish extraction capacity.

The extraction process of the present invention is typically conducted at between about 20° C. to about 400° C., preferably about 20° C. to 200° C. Pressures employed are preferably atmospheric, but elevated pressure may be employed, if necessary, to maintain the hydrocarbon feed in the liquid state.

The amount of salt used in the extraction process is flexible and amounts ranging from about 50 to 400 mass % salt/feed can be employed, preferably 50 to 100 mass %. The actual amounts of salt employed will depend on the amount of aromatics in the feed, the degree of separation desired, the particular characteristics of the salt employed.

The extraction process can be run on a batch or continuous basis, including countercurrent extraction. Procedures such as liquid membrane suspension of the salt can also be employed.

The separation process produces a binary two liquid phase system. The upper, lighter phase is typically the raffinate, of reduced aromatics content and very low salt content. The lower, heavier phase is the extract containing the aromatics-salt clathrate.

Following physical separation of these two liquid phases one from the other by typical techniques such as centrifugation or simple decantation, the salts are released from the aromatics-salt clathrate by the addition of a polar, protic substitution agent such as water, which breaks the clathrate forming a new binary liquid-liquid phase comprising a light-upper phase of hydrocarbon and a heavier, lower phase of salt-water. These phases can be separated by typical liquid-liquid separation procedures again such as centrifugation or decantation. The salt can be recovered from the salt-water phase by distillation or flashing to remove the water. The recovered salt can then be recycled to use. Alternatively, some aromatic-salt clathrates can be declathrated by simply reducing the temperature of the aromatic-salt clathrate from the formation temperature to a reduced temperature, e.g., by cooling from 50° C. down to ambient. As another alternative the araomtic hydrocarbon salt clathrate can be heated to recover the hydrocarbon with the salt being recycled.

The present invention is described and demonstrated in the following non-limiting examples.

EXAMPLES

EXAMPLE 1

A number of salts made by combining 15 cations and 8 anions were synthesized. Their melting points and toluene solubilities were determined and are reported in Table 1.

A number of salts from Table 1, and some not appearing in Table 1 made up of different cation-anion pair combinations were screened using a 1:1 toluene/cyclohexane mixture for their ability to form tolune-salt clathrates in the presence of the non-aromatic cyclohexane. The results are presented below in Table 1A.

TABLE 1

Melting Point (°C.) and Toluene Solubility[1] of Organic Salts (py = pyridinium, pip = piperidinium)

|  | TRIFLUOROACETATE | SALICYLATE | BENZOATE | DIHYDROXYBENZOATE |
|---|---|---|---|---|
| py+ | 78, S | 48, SL | 38, S | 117, S |
| 2-Etpy+ | Liq, S | 47, S | Liq, S | 117, S |
| 3,5-Et$_2$C$_6$H$_3$N+ | Liq, S | 59, S | Liq, S | 180, I |
| 2,4-Me$_2$py+ | 38, S |  |  |  |
| 2,4,6-Me$_3$C$_6$H$_2$H+ | 61, S | 79, S | 49, S | 146, S |
| Quinolinium | 68, S | 71, S | Liq, S | 168, I |
| EtOpy+ | Liq, S | — | — | — |
| pip+ | 28, S | 122, I | — | 196, I |
| Mepip+ | 55, S | 102, S | 62, S | 146, I |
| NEt$_3$H+ | — | 45, S | Liq, S | 34, S |
| NBu$_3$H+ | 41, S | 41, S | Liq, S | 61, S |
| Npr$_3$H+ | 44, S | 45, S | Liq, S | 94, S |
| NMe$_4$+ | 220, I | 141, I | 111, I | 160, I |
| NEt$_4$+ | 65, Sl | 84, I | 42, I | 141, I |
| NBu$_4$+ | 51, S | 87, SL | 54, S | 104, I |

|  | TOLUENE SULFONATE | M-NITROBENZOATE | FORMATE | PHENYL ACETATE |
|---|---|---|---|---|
| py+ | 115, I | 105, S | Liq, I | — |
| 2-Etpy+ | 92, S | — | Liq, S | Liq, S |
| 3,5-Et$_2$C$_6$H$_3$N+ | Liq, I | — | Liq, S | Liq, S |
| 2,4-Me$_2$py+ |  |  |  |  |
| 2,4,6-Me$_3$C$_6$H$_2$H+ | 126, I | 84, S | Liq, S | — |
| Quinolinium | 109, I | 117, S | Liq, S | Liq, S |
| EtOpy+ | — | — | — | — |
| pip+ | 129, SL | 141, S | Liq, I | 99, SL |
| Mepip+ | 92, I | 113, S | Liq, I | Liq, I |
| NEt$_3$H+ | 71, S | 80, S | Liq, I | Liq, S |
| NBu$_3$H+ | 66, S | — | — | — |
| Npr$_3$H+ | 63, S | — | Liq, S | — |
| NMe$_4$+ | 241, I | — | >250, I | — |
| NEt$_4$+ | 106, I | — | Liq, I | — |
| NBu$_4$+ | 72, SL | — | Liq, S | Liq, I |

[1]S = soluble, SL = slightly soluble, I = insoluble

TABLE 1A

Physical Properties of a Range of Liquid Organic Non-Quaternary Low Melting Salts

| Anion | Cation[a] | M.P. °C. | Toluene 20° C. | Toluene 50° C. | Water 20° C. | Water 50° C. | Toluene/Cyclohexane[b] 20° C. | Toluene/Cyclohexane[b] 50° C. | Comments |
|---|---|---|---|---|---|---|---|---|---|
| Benzoate | 1 | 124–127 | SL | S | SL | — | — | precip. 10:5[b] | |
| Benzoate | 2 | 83–86 | I | SL | S | — | — | clear solution | precipitate at 10:40[a] |
| Benzoate | 3 | Liquid | S | — | See Comment | — | cloudy solution | clear solution | possible 2:1 addition? solution at 10:40[a] |
| Benzoate | 4 | Liquid | S | — | I | S | clear solution | clear solution | cyclohexane soluble |
| Benzoate | 5 | Liquid | S | — | I | S | clear solution | clear solution | cyclohexane soluble |
| 2-Hydroxy-benzoate | 1 | 55–60 | I | SL | S | — | clear solution | precip. solution | |
| 2-Hydroxy-benzoate | 2 | 108.5–113 | I | SL | S | — | — | cloudy solution | clathrate at 10:15[a] |
| 2-Hydroxy-benzoate | 3 | 47–62.5 | S | — | S | — | clathrate | clathrate | |
| 2-Hydroxy-benzoate | 4 | Liquid | S | — | I | SL | clear solution | clear solution | cyclohexane soluble |
| 2-Hydroxy-benzoate | 5 | Liquid | S | — | I | I | clear solution | clear solution | cyclohexane soluble |
| Trifluro-acetate | 1 | 99.5–101.5 | I | SL | S | — | — | — | |
| Trifluro-acetate | 2 | 36–38 | I | SL | S | — | cloudy solution | clathrate | |
| Trifluro-acetate | 3 | Liquid | S | — | S | — | clathrate | clathrate | |
| Trifluro-acetate | 4 | Liquid | S | — | I | I | clear solution | clear solution | cyclohexane soluble |
| Trifluro-acetate | 5 | Liquid | S | — | I | I | clear solution | clear solution | cyclohexane soluble |
| Phenyl-acetate | 1 | 118–121 | SL | S | S | — | — | precip. 10:5[b] | |
| Phenyl-acetate | 2 | 98–101 | SL | S | S | — | — | clear solution | precipitate at 10:40[a] |
| Phenyl-acetate | 3 | Liquid | S | — | I | I | clear solution | clear solution | possible 2:1 addition? solution at 10:40[b] |
| Phenyl-acetate | 4 | Liquid | S | — | I | I | clear solution | clear solution | cyclohexane soluble |
| Phenyl-acetate | 5 | Liquid | S | — | I | I | clear solution | clear solution | cyclohexane soluble |
| Diphenyl-acetate | 1 | 146.5–148 | I | SL | S | — | — | — | |
| Diphenyl-acetate | 2 | 158–160.5 | I | I | S | — | — | — | |
| Diphenyl-acetate | 3 | 45–46 | S | — | S | — | clear solution | clear solution | cyclohexane slight solution |
| Diphenyl-acetate | 4 | Liquid | S | — | I | I | clear solution | clear solution | cyclohexane soluble solution |
| Diphenyl-acetate | 5 | Liquid | S | — | I | I | clear solution | clear solution | cyclohexane soluble solution |
| 3-Hydroxy-benzoate | 1 | 177–180 | I | I | I | S | — | — | |
| 3-Hydroxy-benzoate | 2 | 134.5–139 | I | I | S | — | — | — | |
| 3-Hydroxy-benzoate | 3 | 98–101 | I | I | S | — | — | — | |
| 3-Hydroxy-benzoate | 4 | Liquid | I | SL | I | I | — | — | |
| 3-Hydroxy-benzoate | 5 | Liquid | I | SL | I | I | — | — | |
| 4-Hydroxy-benzoate | 1 | 215–217 | I | I | S | — | — | — | |
| 4-Hydroxy-benzoate | 2 | 161.5–169 | I | I | S | — | — | — | |
| 4-Hydroxy-benzoate | 3 | 116–118 | I | I | S | — | — | — | |
| 4-Hydroxy-benzoate | 4 | Liquid | I | I | I | S | — | — | |
| 4-Hydroxy-benzoate | 5 | Liquid | I | SL | I | I | — | — | |
| 2,6-Dihydroxy-benzoate | 1 | 156–157.5 | I | I | I | S | — | — | |
| 2,6-Dihydroxy-benzoate | 2 | 189.5–191 | I | S | I | I | — | — | |
| 2,6-Dihydroxy-benzoate | 3 | 34–35 | S | — | S | — | clathrate 10:5[b] | clathrate 10:5[b] | |
| 2,6-Dihydroxy- | 4 | Liquid | S | — | I | I | clear | clear | cyclohexane soluble |

TABLE 1A-continued

Physical Properties of a Range of Liquid Organic Non-Quaternary Low Melting Salts

| Anion | Cation[a] | M.P. °C. | Toluene 20° C. | Toluene 50° C. | Water 20° C. | Water 50° C. | Toluene/ Cyclohexane[b] 20° C. | Toluene/ Cyclohexane[b] 50° C. | Comments |
|---|---|---|---|---|---|---|---|---|---|
| benzoate | | | | | | | solution | solution | |
| 2,6-Dihydroxy-benzoate | 5 | Liquid | S | — | I | I | clear solution | clear solution | cyclohexane soluble |
| p-Toluene sulfonate | 1 | 180–183 | I | I | S | — | — | — | |
| p-Toluene sulfonate | 2 | 128–129.5 | SL | S | S | — | — | — | |
| p-Toluene sulfonate | 3 | 67–72 | I | I | S | — | — | — | |
| p-Toluene sulfonate | 4 | 40–45* | S | — | S | — | clear solution | clear solution | *v. hygroscopic solution at 10:40[b] |
| p-Toluene sulfonate | 5 | 48–50 | S | — | I | I | clear solution | clear solution | cyclohexane soluble solution at 10:40[b] |
| p-Anisate | 1 | 142–144 | I | SL | S | — | — | — | |
| p-Anisate | 2 | 85–90 | S | — | S | — | — | clear solution | |
| p-Anisate | 3 | | | | | | | | failed to synthesize |
| p-Anisate | 4 | | | | | | | | failed to synthesize |
| p-Anisate | 5 | | | | | | | | failed to synthesize |

[a] 1 = benzylammonium; 2 = piperidinium; 3 = triethylammonium; 4 = trihexylammonium; 5 = trioctylammonium
[b] Toluene cyclohexane 1:1 by volume was used unless otherwise indicated
S = soluble; I = insoluble; SL = slightly soluble The results indicate that organic non-quaternary salts form toluene-salt clathrates but that when the cation contains R radical groups, the sum of the carbons in the total sum of the R radical groups must be less than 16. Without exception, when the cations trihexylammonium and tri-octylammonium produced a salt, the resulting salt was soluble in cyclohexane and in toluene, indicating that the salt is inappropriate for use in aromatics/non-aromatics separations.

EXAMPLE 2

Organic non-quaternary salts were evaluated for their ability to separate varying volumes of 2:1 benzene/cyclohexane solutions at 20° C. and 50° C. The results are listed in Table 2. Mass balances were not recorded.

TABLE 2

Molecular Recognition Characteristics of Liquid Organic Salts by NMR Analysis of 2:1 M Benzene:Cyclohexane

| Amt. Salt | Liquid Phase 20° C. Upper | Liquid Phase Lower | Liquid Phase 50° C. Upper | Liquid Phase Lower |
|---|---|---|---|---|
| Triethylammonium 2,6-dihydroxybenzoate mp: 34–35° C. | | | | |
| 1 g | 1.88:1 | 4.89:1 | 1.88:1 | 3.48:1 |
| 2 g | 1.69:1 | 4.53:1 | 1.72:1 | 6.11:1 |
| 5 g | 1.22:1 | 4.38:1 | 1.37:1 | 3.43:1 |
| Piperidinium triflate m;: 27–29° C. | | | | |
| 1 g | 1.95:1 | 3.00:1 | 1.92:1 | 3.33:1 |
| 2 g | 1.88:1 | 2.63:1 | 1.86:1 | 2.88:1 |
| 5 g | 1.54:1 | 3.39:1 | 1.66:1 | 2.75:1 |
| 2-ethyl pyridinium triflate mp: < 20° C. | | | | |
| 1 g | 1.94:1 | 5.05:1 | 1.86:1 | 3.00:1 |
| 2 g | 1.69:1 | 4.60:1 | 1.81:1 | 2.93:1 |
| 5 g | 1.34:1 | 3.68:1 | 1.43:1 | 2.58:1 |
| Lutidinium triflate mp: < 20° C. | | | | |
| 1 g | 1.90:1 | 5.47:1 | 1.95:1 | 4.64:1 |
| 2 g | 1.73:1 | 4.33:1 | 1.88:1 | 3.64:1 |
| 5 g | 1.38:1 | 3.90:1 | 1.44:1 | 3.09:1 |
| Collidinium triflate mp: 61–62° C. | | | | |
| 1 g | 1.82:1 | 4.76:1 | 1.86:1 | 4.27:1 |
| 2 g | 1.69:1 | 4.64:1 | 1.74:1 | 4.22:1 |
| 5 g | 1.24:1 | 4.08:1 | 1.25:1 | 3.58:1 |
| Pyridinium triflate mp: 73–76° C. | | | | |
| 1 g | Insoluble | 1.88:1 | 6.88:1 | |
| 2 g | Insoluble | 2.00:1 | 5.70:1 | |
| 5 g | | 1.67:1 | 5.00:1 | |

TABLE 2-continued

Molecular Recognition Characteristics of Liquid Organic Salts by NMR Analysis of 2:1 M Benzene:Cyclohexane

| Amt. Salt | Liquid Phase 20° C. Upper | Liquid Phase Lower | Liquid Phase 50° C. Upper | Liquid Phase Lower |
|---|---|---|---|---|
| Tripropylammonium formate mp: < −20° | | | | |
| 2 g | 1.68:1 | 2.91:1 | 1.74:1 | 2.53:1 |
| 1-Methyl piperidinium triflate mp: 53–59° C. | | | | |
| 2 g | Insoluble | | 1.75:1 | 3.80:1 |
| 1-Methyl piperidinium phenylacetate mp: < −20° C. | | | | |
| 2 g | 2.18:1 | 3.91:1 | Soluble | |
| Triethylammonium m-nitrobenzoate mp: 79–81° C. | | | | |
| 2 g | Insoluble | | 1.92:1 | 2.63:1 |
| Quinolinium triflate mp: 67–69° C. | | | | |
| 5 g | Insoluble | | 1.55:1 | 2.86:1 |

From this data it should be noted that selectivities were generally lower at 50° C. than at 20° C. Selectivites also generally decreased as the amount of salt used increased. It was observed that the volume of the liquid clathrate phase tended to be larger at 50° C. than at 20° C.

EXAMPLE 3

A series of organic non-quaternary salts were evaluated on a model feed (Feed A) for selectivity and capacity and compared with N-methylpyrrolidone (NMP) containing various amounts of water for the extraction of the same feed. The feed is described in Table 3.

TABLE 3

| Feed A Component | Mass % |
|---|---|
| Decalin | 49.80 |
| Tetralin | 7.66 |
| Ethylbenzene | 7.74 |
| Mesitylene | 7.63 |
| 1-Methyl Naphthalene | 15.21 |
| Phenanthrene | 11.95 |

The test conditions and results are presented in Table 4.

TABLE 4

Salt and NMP/H₂O Batch Extraction[1] Capacity/Selectivity Results[2] with 25.0 g Feedstock A

| SALT | | RAFFINATE YIELD % (3) | RAFF. SATS + 1RAr, % (4) | UPPER/LOWER PHASE[5] Sats + 1RAr | 2R + Ar | 3RAr |
|---|---|---|---|---|---|---|
| Triethylammonium Salicylate | | 60.8 | 84.02 | 1.59 | 0.34 | 0.30 |
| Lutidinium Triflate | | 65.0 | 82.59 | 1.72 | 0.33 | 0.21 |
| Collidinium Triflate | (a) | 74.8 | 84.38 | 1.72 | 0.28 | 0.26 |
| | (b) | 43.5[6] | 95.73 | 1.88 | 0.09 | 0.04 |
| 2-Ethylpyridinium Triflate | | 77.7 | 80.42 | 1.63 | 0.39 | 0.32 |
| 2-Ethoxypyridinium Triflate | | 91.5 | 78.99 | 1.54 | 0.43 | 0.28 |
| 1-Methylpiperidinium Triflate[7] | | 87.1 | 74.59 | 1.43 | 0.53 | 0.47 |
| Triethylammonium Dihydroxybenzoate | | 44.4[6] | 93.45 | 1.88 | 0.13 | 0.07 |
| Piperidinium Triflate | | 96.0 | 73.17 | 1.22 | 0.67 | 0.67 |
| NMP/10 LV % H₂O | | 40.0 | 90.90 | 1.81 | 0.22 | 0.14 |
| NMP/11 LV % H₂O | | 48.5 | 89.58 | 1.63 | 0.23 | 0.15 |
| NMP/15 LV % H₂O | | 68.7 | 86.80 | 2.54 | 0.20 | 0.13 |
| NMP/18 LV % H₂O | | 69.8 | 84.64 | 1.88 | 0.28 | 0.19 |
| Feedstock | | 100 | 72.84[8] | — | — | — |

[1]Single stage batch extraction with 0.05 mole salt (or 178 LV % Treat NMP/H₂O) at 50° C. unless otherwise noted.
[2]Determined from mass balance and GC analysis.
(3) A measure of extractant capacity.
(4) A measure of lube raffinate quality.
[5]A measure of extractant selectivity.
[6]Used 0.19 mole of salt. Experiment provided a direct comparison with NMP/H₂O results at conditions of equal mass of extractant.
[7]Extraction performed at 70° C.
[8]Theoretical yield of Sats + 1RAr raffinate phase.

As can be seen, extraction using organic non-quaternary salts compares favorably with extraction using NMP/H₂O. Due to solubility problems of the model feed in neat NMP relatively large volumes of water (10 LV % and more) were required in order to observe phase separation.

Both triethyl ammonium dihydroxybenzoate and collidinium triflate have higher selectivities for aromatics than NMP/H₂O. Under conditions of constant treat, temperature and raffinate quality (evidenced by % sats and 1 ring aromatics in raffinate phase), both salts afford a significant yield credit (about 16% and 23% for trielhyammonium dehydroxybenzoate and collidinium triflate respectively at 90%+ sats and 1 ring aromatics in the raffinate phase). Collidinium triflate has the best selectivity for aromatics, in particular 2- and 3- ring aromatics. As compared to NMP/H₂O (at constant mass % treat) collidinium triflate (b) has a greater selectivity for 2R aromatics and 3R aromatics by a factor of about 2.4 and 3.5 respectively, while the selectivity for saturates and 1 ring aromatics is essentially equivalent. It is also seen that as salt treat is increased from 51 to 198 mass %, the salt's selectivity (as measured by % sats and 1 ring aromatics in raffinate) increased from about 84 to 96%.

EXAMPLE 4

Another series of experiments using the organic non-quaternary salts were conducted on a different model feed (Feed B) containing sulfur and nitrogen containing compounds. In addition the effect of adding a polar, protic additive (in this case water) to the salt was evaluated. The feed composition is given in Table 5.

TABLE 5

| Component | Mass % |
|---|---|
| Decalin | 47.05 |
| Tetralin | 7.22 |
| Ethylbenzene | 7.22 |
| Mesitylene | 7.22 |
| 1-Methyl Naphthalene | 14.12 |
| Phenanthrene | 11.29 |
| Collidine | 2.94 |
| Dibenzothiophene | 2.94 |

The conditions of these experimental runs and the results are presented in Table 6.

TABLE 6

Salt Batch Extraction[1] Selectivity Results With 15 g Feedstock B

| | UPPER/LOWER PHASE SATS + 1 RING AROMATICS | | | | | |
|---|---|---|---|---|---|---|
| | Moles of H₂O | | | Moles of H₂O | | |
| Salt | None | 0.015 | 0.03 | None | 0.015 | 0.03 |
| Triethylammonium salicylate[2] | 1.54 | 1.79 | 1.91 | 1.54 | 1.36 | 1.48 |
| Triethylammonium dihydoxybenzoate | 1.83 | 1.94 | 1.79 | 1.83 | 1.67 | 1.77 |
| Collidinium triflate | 1.72 | 1.96 | 2.13 | 1.72 | 0.77 | — |
| Tributylammonium/Toluene Sulfonate | 1.23 | 1.33 | 1.39 | 1.23 | 1.07 | 1.26 |
| Luthidinium triflate | 1.68 | 1.99 | — | 1.68 | 1.62 | — |
| Methylpiperidinium triflate | (3) | 1.33 | 1.41 | (3) | 1.49 | 1.42 |
| Tetrabutylammonium salicylate | (3) | (3) | 1.59 | (3) | 1.35 | 1.41 |

| | UPPER/LOWER PHASE | | | | | | | | |
|---|---|---|---|---|---|---|---|---|---|
| | 2 RING + AROMATICS | | | | | 3 RING AROMATICS | | | |
| | Moles of H₂O | | Moles of H₂O | | Moles of H₂O | | | Moles of NeOH | |
| Salt | None | 0.015 | 0.03 | 0.015 | 0.03 | None | 0.015 | 0.03 | 0.015 | 0.03 |
| Triethylammonium salicylate[2] | 0.38 | 0.35 | 0.38 | 0.42 | 0.38 | 0.26 | 0.24 | .026 | 0.32 | 0.26 |
| Triethylammonium dihydroxybenzoate | 0.31 | 0.33 | 0.36 | 0.34 | 0.29 | 0.20 | 0.22 | 0.24 | 0.23 | 0.19 |
| Collidinium triflate | 0.25 | 0.31 | 0.31 | 0.28 | — | 0.14 | 0.18 | 0.18 | 0.18 | — |
| Tributylammonium | 0.42 | 0.42 | 0.40 | 0.46 | 0.42 | 0.30 | 0.32 | 0.28 | 0.36 | 0.36 |

TABLE 6-continued

| Salt Batch Extraction[1] Selectivity Results With 15 g Feedstock B | | | | | | | | | | |
|---|---|---|---|---|---|---|---|---|---|---|
| p-toluene sulfonate | | | | | | | | | | |
| Lutidinium triflate | 0.31 | 0.32 | — | 0.32 | — | 0.19 | 0.19 | — | 0.21 | — |
| Methylpiperidinium triflate | (3) | 0.54 | 0.54 | 0.43 | 0.46 | (3) | 0.51 | 0.49 | 0.37 | 0.38 |
| Tetrabutylammonium salicylate[5] | (3) | (3) | 0.37[4] | 0.38 | 0.38 | (3) | (3) | 0.25 | 0.26 | 0.26 |

[1] Single stage batch extraction with 0.03 mole salt at 50° C.
[2] 0.025 and 0.050 moles of water used; 25 grams of feedstock B
(3) Salt failed to dissolve at 50° C.
[4] 0.034 moles of water used
[5] Comparative compound embraced by U.S. Pat. No. 4,359,596

From this it is clear that the process of the present invention using organic non-quaternary salts to selectivity extract aromatics from streams containing aromatics and non-aromatics is affected by the presence of water. The salt selectivity for saturates and 1 ring aromatics generally increases with increasing water content whereas the selectivity for 2 ring+ and 3 ring aromatics is either equivalent or worse than that for the salt under dry conditions. These results are similar to those observed with NMP/H$_2$O in Table 4 where increasing water content increased the selectivity for saturates and 1 ring aromatics in the upper raffinate phase.

As shown in Table 7, increasing the salt's water content decreases the salt's capacity while increasing its selectivity in a similar fashion as that for NMP/H$_2$O.

TABLE 7

| Effect of Water Additive Concentration on Salt Capacity[1] | | | | | | |
|---|---|---|---|---|---|---|
| | Mass of Feedstock Extracted, g | | | Raffinate Yield, % | | |
| | moles of H$_2$O | | | moles of H$_2$O | | |
| Salt | Dry | 0.015 | 0.03 | Dry | 0.015 | 0.03 |
| Triethylammonium salicylate[3] | 5.73 | 3.53 | 2.48 | 62 | 76 | 83 |
| Lutidinium triflate | 4.41 | 3.17 | n.d. | 71 | 79 | n.d. |
| Collidinium triflate | 4.78 | 3.72 | 3.01 | 68 | 75 | 80 |
| 1-Methylpiperidinium triflate | (2) | 2.75 | 1.62 | (2) | 83 | 89 |
| Triethylammonium dihydroxybenzoate | 4.26 | 3.04 | 3.55 | 71 | 80 | 86 |

[1] All single stage batch extraction experiments carried out with 15.0 g of model feedstock B, 0.030 mole salt at 50° C.
[2] Salt failed to dissolve at 50° C. under dry conditions
[3] Used 25 grams of Feedstock B with 0.05 mole salt at 50° C.

This reduction in salt capacity with increasing water content can be exploited as a means for breaking the clathrate, thereby springing the aromatic molecules from the salt and regenerating the salt for reuse.

Tests conducted with methanol and ethanol were less consistent than those employing water as the additive but tended to go in the opposite direction, i.e., increased capacity with no or negative impact on selectivity.

EXAMPLE 5

The organic non-quaternary salt triethylammonium salicylate was compared with single-stage NMP extraction on three lube oil samples. The triethylammonium salicylate was placed in a vacuum desiccator and dried for several days before use. The salt was kept in the desiccator when not in use because of its hygroscopic properties. The object was to produce raffinates of similar Refractive Index by NMP extraction and liquid salt complexation. The lube oils treated were a 60N, a 210N and an extracted 150N base oil. All were non-waxy. The condition employed and result obtained are presented in Tables 8A. 8B and 8C.

TABLE 8A

| Data Summary For Triethylammonium Salicylate Liquid Clathrate Experiments | | | | |
|---|---|---|---|---|
| Feed | Baytown 60N Coatal Distillate | | | |
| Extraction Run # | A | B | C | D |
| Solvent Used | LC | LC | LC | LC |
| Temperature (C.) | 65 | 65 | 65 | 65 |
| Treat (wt %) | 24.0 | 48.0 | 71.9 | 119.8 |
| H$_2$O in Solvent (lv %) | 0 | 0 | 0 | 0 |
| Feed RI | 1.4730 | 1.4730 | 1.4730 | 1.4730 |
| Feed Density 15C | 0.8970 | 0.8970 | 0.8970 | 0.8970 |
| Feed Used (gms) | 25.02 | 25.02 | 25.05 | 25.06 |
| Raffinate RI | 1.4711 | 1.4696 | 1.4678 | 1.4662 |
| Raffinate Density 15C | 0.8942 | 0.8918 | 0.8898 | 0.8873 |
| Raffinate Recovered (gms) | 20.96 | 21.25 | 20.35 | 20.06 |
| Extract RI | 1.5101 | 1.5158 | 1.5131 | 1.5354 |
| Extract Density 15C | N/A | N/A | 0.9543 | 1.0231 |
| Extract Recovered (gms) | 0.99 | 1.85 | 2.84 | 3.80 |
| Yield RI (lv %) | 95.13 | 92.64 | 88.52 | 90.17 |
| Yield Density (lv %) | N/A | N/A | 88.84 | 92.86 |
| Yield (wt %, Rec weights) | 95.49 | 91.99 | 87.75 | 84.07 |
| (lv % calculated) | 95.79 | 92.53 | 88.46 | 84.99 |
| Average lv % yield | 95.46 | 92.58 | 88.61 | 89.34 |
| Base Case NMP Single Stage Batch Extractions | | | | |
| Feed | Baytown 60N Coastal Distillate | | | |
| Extraction Run # | 1 | 2 | 3 | 4 |
| Solvent Used | NMP | NMP | NMP | NMP |
| Temperature (C.) | 65 | 50 | 65 | 65 |
| Treat (wt %) | 56.72 | 58.46 | 116.57 | 172.85 |
| H$_2$O in Solvent (lv %) | 2 | 2 | 2 | 2 |
| Raffinate RI | 1.4684 | 1.4672 | 1.4629 | 1.4593 |
| Raffinate Density 15C | 0.8917 | 0.8896 | 0.8825 | 0.8775 |
| Raffinate Recovered (gms) | 147.25 | 141.16 | 117.63 | 93.42 |
| Extract RI | 1.5069 | 1.5155 | 1.4978 | 1.4939 |
| Extract Density 15C | 0.9475 | 0.9571 | 0.9391 | 0.9328 |
| Extract Recovered (gms) | 22.28 | 16.73 | 52.97 | 71.05 |
| Yield RI (lv %) | 88.05 | 87.99 | 71.06 | 60.40 |
| Yield Density (lv %) | 90.50 | 89.04 | 74.38 | 64.74 |
| Yield (wt %, Rec weights) | 86.86 | 89.40 | 68.95 | 56.80 |
| (lv % calculated) | 87.37 | 90.15 | 70.08 | 58.06 |
| Average lv % yield | 88.64 | 87.99 | 71.84 | 61.07 |

TABLE 8B

| Data Summary For Triethylammonium Silicylate Liquid Clathrate Experiments | | | | | |
|---|---|---|---|---|---|
| Feed | Baytown 250N Coastal Distillate | | | | |
| Extraction Run # | E | F | G | H | I |
| Solvent Used | LC | LC | LC | LC | LC |

TABLE 8B-continued

Data Summary For Triethylammonium Silicylate Liquid Clathrate Experiments

| | | | | | |
|---|---|---|---|---|---|
| Temperature (C.) | 65 | 65 | 65 | 65 | 85 |
| Treat (wt %) | 50.28 | 100.00 | 149.96 | 299.60 | 149.84 |
| H2O in Solvent (lv %) | 0 | 0 | 0 | 0 | 0 |
| Feed RI | 1.4900 | 1.4900 | 1.4900 | 1.4900 | 1.49 |
| Feed Density 15C | 0.9247 | 0.9247 | 0.9247 | 0.9247 | 0.9247 |
| Feed Saturates (wt %) | 54.30 | 54.30 | 54.30 | 54.30 | 54.30 |
| Feed Aromatics (wt %) | 45.70 | 45.70 | 45.70 | 45.70 | 45.70 |
| Feed Used (gms) | 25.06 | 25.01 | 25.00 | 20.00 | 20.00 |
| Raffinate RI | 1.4856 | 1.4831 | 1.4812 | 1.4776 | 1.4814 |
| Raffinate Density 15C | 0.9196 | 0.9162 | 0.9135 | 0.9089 | 0.9141 |
| Raffinate Saturates (wt %) | 57.0 | N/A | N/A | N/A | N/A |
| Raffinate Aromatics (wt %) | 43.0 | N/A | N/A | N/A | N/A |
| Raffinate Recovered (gms) | 22.55 | 20.83 | 21.32 | 15.52 | 21.76 |
| Extract RI | 1.5583 | 1.5349 | 1.5448 | 1.5388 | 1.5486 |
| Extract Density 15C | N/A | 1.0145 | 1.0397 | 1.0202 | 1.0631 |
| Extract Recovered (gms) | 1.82 | 3.54 | 4.15 | 4.72 | 4.07 |
| Yield RI (lv %) | 93.95 | 86.68 | 86.16 | 79.74 | 87.20 |
| Yield Density (lv %) | N/A | 91.35 | 01.13 | 85.80 | 92.89 |
| average lv % | 93.95 | 89.02 | 88.64 | 82.77 | 90.04 |
| Yield (wt %, Rec weights) | 92.53 | 85.47 | 83.71 | 76.68 | 84.24 |
| (lv % calculated) | 93.04 | 86.27 | 84.73 | 78.01 | 85.22 |
| Average lv % yield | 93.50 | 88.10 | 87.34 | 81.19 | 88.44 |

Base Case NMP Singel Stage Batch Extractions

| | | | | | |
|---|---|---|---|---|---|
| Feed | | Baytown 250N Coastal Distillate | | | |
| Extraction Run # | 5 | 6 | 7 | 8 | |
| Solvent Used | NMP | NMP | NMP | NMP | |
| Temperature (C.) | 65 | 65 | 65 | 50 | |
| Treat (wt %) | 50.07 | 99.57 | 150.02 | 299.75 | |
| H2O in Solvent (lv %) | 2 | 2 | 2 | 2 | |
| Raffinate RI | 1.4848 | 1.4789 | 1.4756 | 1.4701 | |
| Raffinate Density 15C | 0.9188 | 0.9097 | 0.9047 | 0.8973 | |
| Raffinate Saturates (wt %) | 67.1 | N/A | N/A | N/A | |
| Raffinate Aromatics (wt %) | 32.9 | N/A | N/A | N/A | |
| Raffinate Recovered (gms) | 224.55 | 205.03 | 170.29 | 121.13 | |
| Extract RI | 1.5374 | 1.5295 | 1.5251 | 1.5264 | |
| Extract Density 15C | 0.9896 | 0.9796 | 0.9743 | 0.9766 | |
| Extract Saturates (wt %) | 18.1 | N/A | N/A | N/A | |
| Extract Aromatics (wt %) | 81.9 | N/A | N/A | N/A | |
| Extract Recovered (gms) | 24.87 | 43.14 | 74.91 | 75.75 | |
| Yield RI (lv %) | 90.11 | 78.06 | 70.91 | 64.65 | |
| Yield Density (lv %) | 91.67 | 78.54 | 71.26 | 65.45 | |
| average lv % | 90.11 | 78.06 | 71.09 | 65.05 | |
| Yield (wt %, Rec weights) | 90.03 | 82.62 | 69.45 | 61.84 | |
| (lv % calculated) | 90.61 | 83.98 | 70.98 | 63.73 | |
| Average lv % yield | 90.80 | 80.19 | 71.05 | 64.61 | |

TABLE 8C

Date Summary For Triethylammonium Salicylate Liquid Clathrate Experiments

| Feed | 150N Base Oil | | |
|---|---|---|---|
| Extraction Run # | 9 | 10 | 11 |
| Solvent Used | LC | LC | LC |
| Temperature (C.) | 65 | 65 | 65 |
| Treat (wt %) | 49.96 | 100.12 | 149.80 |
| H2O in Solvent (lv %) | 0 | 0 | 0 |
| Feed RI | 1.4586 | 1.4586 | 1.4586 |
| Feed Density 15C | 0.8752 | 0.8752 | 0.8752 |
| Feed Viscosity @ 40° C. | 29.026 | 29.026 | 29.026 |
| Feed Viscosity @ 100° C. | 4.959 | 4.959 | 4.959 |
| Feed Viscosity Index | 91.9 | 91.9 | 91.9 |
| Feed Used (gms) | 25.06 | 25.01 | 25.02 |
| Raffinate RI | 1.4582 | 1.4578 | 1.4579 |
| Raffinate Density 15C | 0.8748 | 0.8741 | 0.8739 |
| Raffinate Viscosity @ 40° C. | 29.087 | N/A | 28.911 |
| Raffinate Viscosity @ 100° C. | 4.967 | N/A | 4.957 |
| Raffinate Viscosity Index | 92.2 | N/A | 92.7 |
| Raffinate Recovered (gms) | 24.72 | 24.15 | 23.10 |
| Extract RI | N/A | N/A | 1.5295 |
| Extract Density 15C | N/A | N/A | N/A |
| Extract Recovered (gms) | 0.60 | 0.86 | 1.03 |
| Yield RI (lv %) | N/A | N/A | 99.02 |
| Yield Density (lv %) | N/A | N/A | N/A |
| average lv % | N/A | N/A | 99.02 |
| Yield (wt %, Rec weights) | 97.63 | 96.56 | 95.73 |
| (lv % calculated) | 97.67 | 96.68 | 95.87 |
| Average lv % yield | 97.67 | 96.68 | 95.87 |

Base Case NMP Single Stage Batch Extractions

| Feed | MCT-10 Base Oil | | |
|---|---|---|---|
| Extraction Run # | BE-24-89 | BE-25-89 | BE-26-89 |
| Solvent Used | NMP | NMP | NMP |
| Temperature (C.) | 65 | 65 | 65 |
| Treat (wt %) | 49.51 | 99.92 | 150.16 |
| H2O in Solvent (lv %) | 2 | 2 | 2 |
| Raffinate RI | 1.4576 | 1.4572 | 1.4565 |
| Raffinate Density 15C | 0.8740 | 0.8727 | 0.8717 |
| Raffinate Viscosity @ 40° C. | 28.710 | N/A | 28.326 |
| Raffinate Viscosity @ 100° C. | 4.937 | N/A | 4.923 |
| Raffinate Viscosity Index | 92.7 | N/A | 94.8 |
| Raffinate Recovered (gms) | 196.48 | 188.49 | 182.89 |
| Extract RI | 1.4952 | 1.4884 | 1.4861 |
| Extract Density 15C | 0.9290 | 0.9262 | 0.9176 |
| Extract Recovered (gms) | 4.19 | 10.90 | 15.33 |
| Yield RI (lv %) | 97.34 | 95.51 | 92.91 |
| Yield Density (lv %) | 97.82 | 95.33 | 92.37 |
| average lv % | 97.34 | 95.51 | 92.64 |

TABLE 8C-continued

Date Summary For Triethylammonium Salicylate Liquid Clathrate Experiments

| | | | |
|---|---|---|---|
| Yield (wt %, Rec weights) | 97.91 | 94.53 | 92.27 |
| (lv % calculated) | 98.05 | 94.80 | 92.64 |
| Average lv % yield | 97.69 | 95.16 | 92.64 |

The extraction using the salt was conducted in the following manner.

A small temperature regulated batch extraction vessel was used as the separation device. A known weight of distillate was placed in the vessel and allowed to equilibrate to the desired reaction temperature.

Next, a known weight of the solid crystalline salt (dependent on the desired treat) was placed in the extraction vessel and allowed to warm up to the reaction temperature. As the mixture was warming, the crystals began to melt or dissolve in the oil. After about 5 minutes about half the crystals had dissolved. When all of the salt had dissolved, a small perforated plate or screen suspended by a wire was used to mix the oil and liquid salt together. The mixing rate was 100 strokes in one minute. When the mixing was stopped, the emulsion of small beak-like bubbles started to settle to form two distinct phases. The two phases were completely settled after 5 minutes. The two phases were remixed as above and allowed to resettle ensuring complte and intimate contacing.

The lower or extract phase was drained from the batch extractor into a preweighed separatory funnel. The weight of the sep-funnel and extract solution were recorded on the run sheets. The extract solution was then washed in the sep-funnel with a known weight of water (~70 cc). The mixture was well shaken three times and vented and allowed to settle after each shaking. This procedure disengaged the clathrate from the oil and formed an emulsion. Caution should be exercised at this point for this reaction is somewhat exothermic. To free the oil phase from the emulsion, a known weight of toluene (20 cc) was added, shaken and allowed to settle. The lower phase (clathrate and water) was drained off into a second preweighed sepfunnel. The above washing procedure was repeated noting all the weights and combining all the water phases in the second sep-funnel. The sep-funnel containing the water phases was then washed twice with known weights of toluene (20ccx2) to remove any trapped organics in the water. The organic phases were added back to the organics in the other sep-funnel. Finally, the sep-funnel containing the water phase was drained into a preweighed stripping flask, reweighed and stripped on a rotovap until all the water and residual toluene were removed. The flask was then reweighed and the contents were analyzed for refractive index and density. The sep-funnel containing the organic material was also weighed, stripped and the oil analyzed for Refractive Index and Density.

The upper phase left in the batch extraction vessel (raffinate solution) was drained into a preweighed sepfunnel. The solution and funnel were reweighed, then a known weight of water (20 cc) was added. The mixture was shaken and allowed to settle (three times). The reaction was probably exothermic but was not noticeable, indicating a very small amount of liquid salt was present. An emulsion was formed as with the extract. A known amount of hexane was added (20 cc) to break the emulsion after shaking. The water and liquid salt or lower phase was drained to a second preweighed sep-funnel, reweighed and the washing procedure repeated. The water washings were combined and washed twice with hexane (20 ccx2) to remove any trapped organic material. All of the organic phases were combined in one sep-funnel while all of the water phases were combined in the other sep-funnel. The contents of each sep-funnel were drained into one of two preweighed stripping flasks. These flasks were then weighed again, then the water or hexane was removed by rotovap stripping. When this process was complete, the flasks were reweighed and the contents analyzed for Refractive Index and Density.

The runs conducted on the extraced 150 N and base oil shows a yield debit. Correction for equal treat would further increase the debit, and suggest that the clalhrate is less suitable for the final stages of extraction where mainly highly alkylated one or 2 ring aromatics remain to be removed. No RI or density yields could be obtained with the clathrate.

As is seen, triethylammonium salicylate shows up to a 4% yield credit at equal raffinate RI when used on the 60N and 250N oils. A high treat is required for the clathrate to obtain this quality. If the NMP operating temperature were lowered to obtain the same quality product at the same treat level as with the clathrate (i.e., at the same capacity) the NMP selectivity would improve and it is estimated that the yield credit for the clathrate would be about 1% on feed.

What is claimed is:

1. A method for separating hydrocarbon feed streams containing mixtures of aromatic hydrocarbons and non-aromatic hydrocarbons into aromatics lean raffinate streams and aromatics rich extract streams by contacting the hydrocarbon feed streams with an organic non-quaternary clathrate salt having less than 16 carbon atoms in the cation, whereby the clathrate salt selectively interacts with the aromatic component of the hydrocarbon feed mixture producing a raffinate phase of reduced aromatic content a hydrocarbon - salt clathrate and an extract phase of increased aromatic content containing the clathrate salt and combined aromatic hydrocarbon, separating the raffinate phase from the extract phase and releasing the aromatic hydrocarbon from the clathrate salt of the extract phase to recover an aromatics rich stream and the organic non-quaternary salt which is recycled for contact with fresh hydrocarbon feed.

2. The method of claim 1 wherein the contacting of the organic non-quaternary clathrate salt with the hydrocarbon feed is conducted at temperatures above the melting point of the salt but below the decomposition temperature of either the salt or the hydrocarbon feed.

3. The method of claim 1 wherein the organic non-quaternary clathrate salt is used in amounts ranging from about 50 to 400 mass % salt to feed.

4. The method of claim 1 wherein the contacting of the clathrate salt and the hydrocarbon feed is counter-current.

5. The method of claim 1 wherein the raffinate phase is separated from the extract phase by decantation.

6. The method of claim 1 wherein the aromatic hydrocarbon is released from the hydrocarbon - salt clathrate extract phase by the addition of a polar, protic substitution agent.

7. The method of claim 1, 2, 3, 4, 5 or 6 wherein the organic non-quaternary clathrate salt is selected from the following:

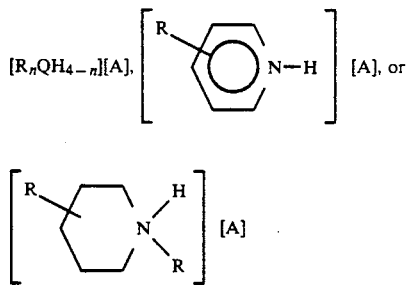

wherein

Q is nitrogen, phosphorus, or arsenic;

R is hydrogen, $C_1$–$C_{12}$ linear or branched alkyl, $C_5$–$C_{12}$ cycloalkyl, $C_7$–$C_{12}$ aralkyl or alkaryl, and $C_6$–$C_{10}$ aryl, including inert or unreactive substances including heteroatom containing species, and mixtures thereof, wherein the total number of carbon atoms in the sum of the R radical groups is less than 16;

n is an integer ranging from 1–3;

A is a monovalent or polyvalent anion.

8. The method of claim 7 wherein the cation of the organic non-quaternary clathrate salt is selected from the group consisting of triethylammonium, lutidinium, collidinium, 2-ethyl pyridinium, 2-thoxy pyridinium, 1-methyl piperidinium, piperidinium, 1-ethyl collidinium, 1-methyl, 3-ethyl imidazolium, 1 methylimidazolium.

9. The method of claim 7 wherein the anion of the organic non-quaternary clathrate salt is selected from the group consisting of carboxylates, benzoates, sulfonates, naphthenate, bicarbonate, bisulfide, nitrate, halometallate, phosphonate, borate, acetate, hydroxide, methoxide, phenoxide, fluoride, chloride, bromide, and iodide.

10. The method of claim 7 wherein the organic non-quaternary clathrate salt is selected from the group consisting of triethylammonium salicylate, lutidinium triflate, collidinium triflate, 2-ethyl pyridinium triflate, 2-ethoxy pyridinium triflate, 1-methyl piperidinium triflate, triethyl ammonium 2, 6-dihydroxybenzoate, piperidinium triflate, tripropyl ammonium formate, 1-methyl piperidinium phenyl acetate, tri ethyl ammonium m-nitrobenzoate, quinolinium triflate.

* * * * *